US012637652B2

(12) United States Patent
D'Apuzzo et al.

(10) Patent No.: US 12,637,652 B2
(45) Date of Patent: May 26, 2026

(54) MEASURING DEFORMABILITY OF A CELL

(71) Applicant: HEWLETT-PACKARD DEVELOPMENT COMPANY, L.P., Spring, TX (US)

(72) Inventors: Fausto D'Apuzzo, Palo Alto, CA (US); Viktor Shkolnikov, Palo Alto, CA (US); Alexander Govyadinov, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 820 days.

(21) Appl. No.: 17/912,723

(22) PCT Filed: Apr. 23, 2020

(86) PCT No.: PCT/US2020/029528
§ 371 (c)(1),
(2) Date: Sep. 19, 2022

(87) PCT Pub. No.: WO2021/216070
PCT Pub. Date: Oct. 28, 2021

(65) Prior Publication Data
US 2023/0140317 A1     May 4, 2023

(51) Int. Cl.
*C12M 1/34* (2006.01)
*C12M 3/06* (2006.01)

(52) U.S. Cl.
CPC ............ *C12M 41/46* (2013.01); *C12M 23/16* (2013.01); *G01N 2203/0092* (2013.01)

(58) Field of Classification Search
None
See application file for complete search history.

(56) References Cited

U.S. PATENT DOCUMENTS

| | | |
|---|---|---|
| 7,578,171 B2 | 8/2009 | Manneville |
| 10,453,192 B2 | 10/2019 | Hattori et al. |
| 10,488,396 B2 | 11/2019 | Sacchetti et al. |
| 2002/0042125 A1 | 4/2002 | Petersen et al. |

(Continued)

FOREIGN PATENT DOCUMENTS

| | | | |
|---|---|---|---|
| CN | 109395261 A | 3/2019 | |
| CN | 109827890 A | 5/2019 | |
| WO | WO-2014006145 A1 * | 1/2014 | ......... G01N 15/1456 |

OTHER PUBLICATIONS

Silva et al., Acoustic deformation for the extraction of mechanical properties of lipid vesicle populations, Jun. 24, 2019, Phys. Rev. E 99, 063002 (Year: 2019).*

(Continued)

*Primary Examiner* — Holly Kipouros
(74) *Attorney, Agent, or Firm* — Foley & Lardner LLP

(57) ABSTRACT

An example method for measuring deformability of a cell, consistent with the present disclosure, includes detecting a single cell of a biologic sample in a cell probing chamber of a microfluidic device. The method includes isolating the cell in the cell probing chamber of the microfluidic device by terminating the flow of the biologic sample through the microfluidic device. The method further includes causing deformation of the cell by introducing ultrasonic waves into the cell probing chamber, and measuring deformability of the cell responsive to the introduction of the ultrasonic waves.

10 Claims, 11 Drawing Sheets

(56) References Cited

U.S. PATENT DOCUMENTS

| | | |
|---|---|---|
| 2009/0098541 A1 | 4/2009 | Southern et al. |
| 2013/0171685 A1* | 7/2013 | Schutze ............... G03H 1/0443 |
| | | 435/288.7 |
| 2019/0071695 A1 | 3/2019 | Wagner et al. |
| 2020/0164369 A1* | 5/2020 | Li ..................... B01L 3/502707 |
| 2021/0101115 A1* | 4/2021 | Iizuka .................... G01N 27/00 |
| 2021/0394182 A1* | 12/2021 | Sarioglu ........... B01L 3/502761 |
| 2024/0052284 A1* | 2/2024 | Gachelin ............... C12M 41/36 |

OTHER PUBLICATIONS

Yang et al., A comprehensive strategy for the analysis of acoustic compressibility and optical deformability on single cells, Apr. 4, 2016, Scientific Reports, 6:23946 (Year: 2016).*
Link et al., Acoustic erythrocytometer for mechanically probing cell viscoelasticity, Apr. 21, 2020, Lab Chip, 20, 1991 (Year: 2020).*

* cited by examiner

223

225

227

221

202

217-2

217-2

219

ULTRASOUND
CONTROLLER

MEASURING DEFORMABILITY OF A CELL

CROSS-REFERENCE TO RELATED APPLICATIONS

This Utility Patent Application is a U.S. National Stage filing under 35 U.S.C. § 371 of PCT/US2020/029528, filed Apr. 23, 2020, incorporated by reference herein.

BACKGROUND

Cellular mechanical properties may be indicative of various diseases states. For example, a change in the deformability of red blood cells is an early indication of sepsis as well as hereditary disorders such as spherocytosis, elliptocytosis, ovalocytosis, and stomatocytosis, metabolic disorders such as diabetes, hypercholesterolemia, and obesity, as well as other disorders such as adenosine triphosphate-induced membrane changes, oxidative stress, and paroxysmal nocturnal hemoglobinuria. A change in red blood cell deformability is also associated with malaria, sickle cell anemia, and myocardial infarction. As a further example, change in deformability of white blood cells has also been associated with sepsis.

Rheological phenotyping, or the characterization of the deformability of cells, allows for detection of various diseases. In cancer research, elasticity of circulating tumor cells is strongly correlated the metastatic potential of the cells, with more elastic cells having higher metastatic potential.

DETAILED DESCRIPTION

Figure 1:
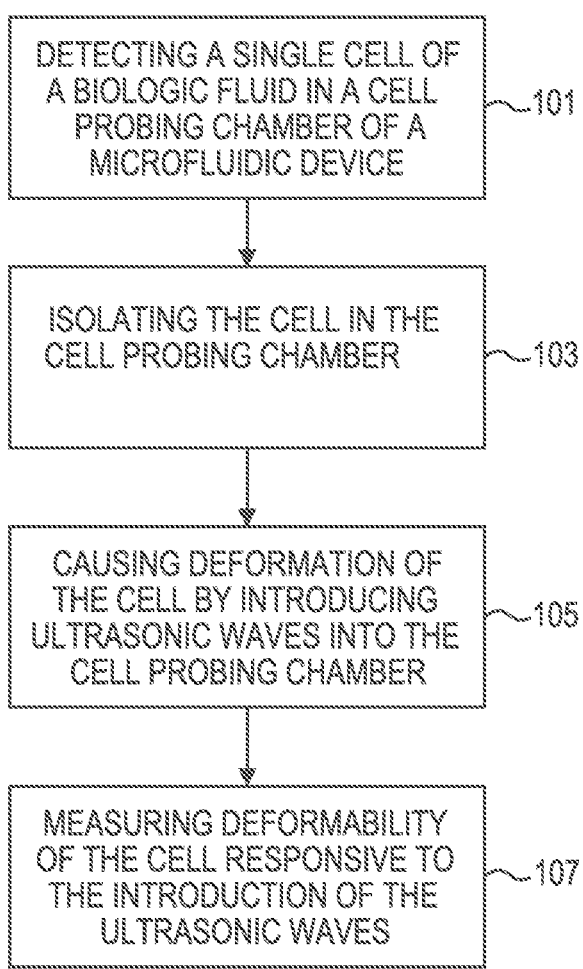
FIG. 1 illustrates an example method for measuring deformability of a cell, consistent with the present disclosure.

In the following detailed description, reference is made to the accompanying drawings which form a part hereof, and in which is shown by way of illustration specific examples in which the disclosure may be practiced. It is to be understood that other examples may be utilized, and structural or logical changes may be made without departing from the scope of the present disclosure. The following detailed description, therefore, is not to be taken in a limiting sense, and the scope of the present disclosure is defined by the appended claims. It is to be understood that features of the various examples described herein may be combined, in part or whole, with each other, unless specifically noted otherwise.

Biological cells are the basic building blocks of skin, tissues, and other materials. Cells and their organelles are enveloped by thin membranes that separate their chemical contents from the extracellular environment. Biological membranes are supramolecular assemblies composed of a lipid double layer with embedded and adsorbed membrane proteins. Each monolayer of the membrane consists of billions of adjacent lipid molecules, which are composed of two hydrophobic tails and a hydrophilic headgroup. The two monolayers taken together, facing each other with the hydrophobic tails, serve as a barrier of 4-10 nm thickness, which exhibits a partial permeability to some small hydrophobic and polar molecules.

Cell deformation and mechanical property analysis may allow for rheological phenotyping. For instance, cells may be brought into an apparatus and deformed. The flow may be driven by external pumps, and the deformation of the cell may be observed via a high-speed camera. The deformation is obtained later by post-processing. Post-processing of a large number of optical images takes a significant amount of time. Moreover, these devices are not able to sort the cells, as they cannot operate in real time. Furthermore, these devices take hours to process a large amount of cells (such as greater than 10^6 cells) and are poorly amenable to point-of-care instrument solutions.

Measuring deformability of a cell, consistent with examples of the present disclosure, may include isolating a cell in a cell probing chamber, and measuring deformability of the cell with either integrated optics or an external imaging system. By applying a standing pressure wave to the cell within the cell probing chamber, an imaging system that operates at relatively low speed, such systems that capture approximately 10 frames per second (fps), may be used rather than relatively higher speed imaging systems, such as those that capture approximately 1000 fps or more. By allowing for slower fps imaging systems to be used, the cost for conducting rheological phenotyping may be reduced, and analytic rheological phenotyping may be performed on a single cell at a time.

An example method for measuring deformability of a cell, consistent with the present disclosure, includes detecting a single cell of a biologic sample in a cell probing chamber of a microfluidic device. The method includes isolating the cell in the cell probing chamber of the microfluidic device by terminating the flow of the biologic sample through the microfluidic device. The method further includes causing deformation of the cell by introducing ultrasonic waves (e.g., standing waves) into the cell probing chamber and measuring deformability of the cell responsive to the introduction of the ultrasonic waves.

In additional examples of the present disclosure, an apparatus for measuring deformability of a cell includes a fluidic channel actuated by a set of fluidic pumps. The apparatus may further include a cell probing chamber to hold a single cell from a biologic sample for deformation testing. The apparatus may further include an ultrasound source to perform deformation testing on the cell by applying a pressure field to the cell in the cell probing chamber. In various examples, the apparatus includes a lateral fluidic channel and a longitudinal fluidic channel disposed orthogonal to the lateral fluidic channel. Each of the lateral fluidic channel and the longitudinal fluidic channel are actuated by a different respective set of fluidic pumps. In such examples, the apparatus includes a cell probing chamber disposed at an intersection of the lateral fluidic channel and the longitudinal fluidic channel.

In yet a further example, an apparatus for measuring the deformability of a cell, consistent with the present disclosure, includes a lateral fluidic channel and a longitudinal fluidic channel disposed orthogonal to the lateral fluidic channel. Each of the lateral fluidic channel and the longitudinal fluidic channel are actuated by a different respective set of fluidic pumps. The apparatus may further include a cell probing chamber disposed at an intersection of the lateral fluidic channel and the longitudinal fluidic channel. The cell probing chamber may hold a single cell from a biologic sample for deformation testing. Moreover, the apparatus may include an ultrasound source to perform deformation testing on the cell by applying a pressure field to the cell in the cell probing chamber, and a plurality of channels fluidically coupled to the cell probing chamber to sort cells after deformation testing.

Turning now to the Figures, FIG. 1 illustrates an example method 100 for measuring deformability of a cell, consistent with the present disclosure. At 101, the method 100 includes detecting a single cell of a biologic sample in a cell probing chamber of a microfluidic device. As discussed further herein, flow within the microfluidic device may be controlled using a plurality of pumps, and an imaging system may be used to visualize cells within the microfluidic device. The microfluidic device includes a channel that is actuated by a set of pumps. In various examples, the microfluidic device may include a cross-channel which is actuated in two directions by an independent set of pumps. In the flow direction, flow is provided either on-chip or off-chip by traditional pumps. Once a cell is identified within the microfluidic device, the pumps may stop pumping and therefore stop the flow of fluid through the microfluidic device. Accordingly, at 103, the method 100 includes isolating the cell in the cell probing chamber of the microfluidic device by terminating the flow of the biologic sample through the microfluidic device.

At 105, the method 100 further includes causing deformation of the cell by introducing ultrasonic waves into the cell probing chamber. For instance, an ultrasonic pressure field may be generated, such that the ultrasonic waves apply pressure on the isolated cell. In various examples, the microfluidic device provides a structured pressure field by producing standing pressure-waves with micron-scale wavelengths. For instance, high-frequency piezo inkjet (PIJ) actuators may be fired simultaneously with semi-periodic pulses to create a standing pressure-wave in the chamber. Examples are not so limited, however, and in some examples, introducing ultrasonic waves includes generating an ultrasonic pressure field using an ultrasonic transducer external to the microfluidic device. In such examples, the method may include focusing the ultrasonic waves using an ultrasonic horn, and delivering the focused ultrasonic waves to a via opening in the microfluidic device.

As discussed further herein, the microfluidic device may include a transparent surface that allows imaging, such as by epi-illumination microscopy. Accordingly, at 107 the method 100 includes measuring deformability of the cell responsive to the introduction of the ultrasonic waves. For instance, the method may include measuring the width and/or length of the cell before application of the ultrasonic waves, and measuring the width and/or length of the cell during application of the ultrasonic waves.

In various examples, the method 100 may include releasing the cell from the cell probing chamber by asymmetrically activating a plurality of fluidic pumps in the microfluidic device.

Figure 2:
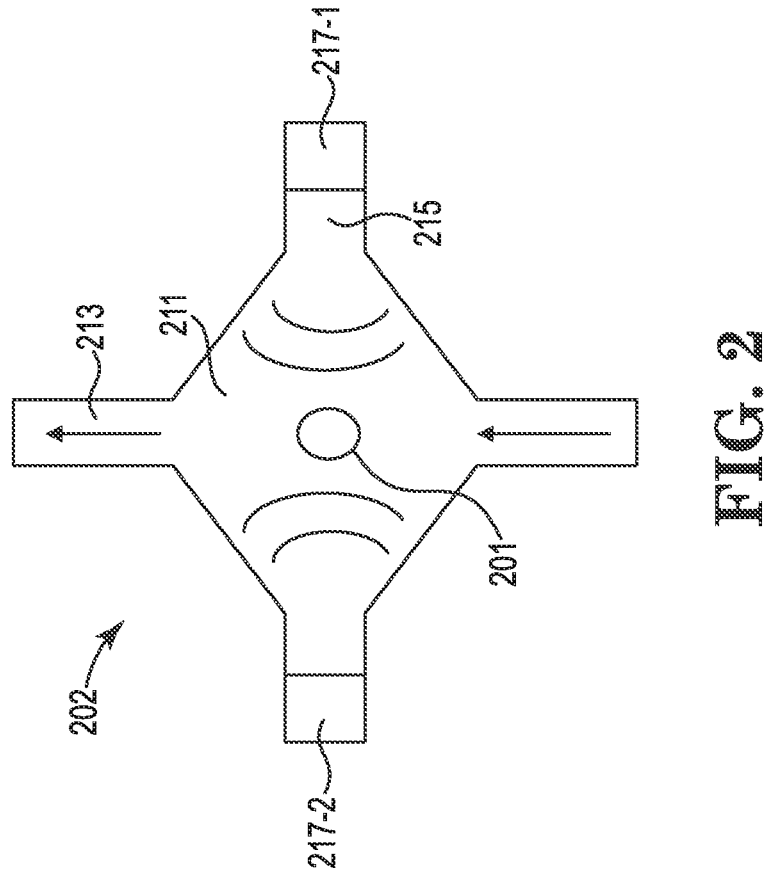
FIG. 2 illustrates an example apparatus for measuring deformability of a cell, consistent with the present disclosure.

FIG. 2 illustrates an example apparatus 202 for measuring deformability of a cell, consistent with the present disclosure. The apparatus 202 is capable of performing the method 100 illustrated in FIG. 1. For instance, the apparatus 202 is capable of detecting a single cell 209 of a biologic sample in a cell probing chamber 211 of a microfluidic device 202. A biologic sample may flow through channel 213 in the direction of the arrows. As discussed further herein, the fluid flow may be induced using internal pumps and/or external pumps. Accordingly, the cell 109 may be isolated in the cell probing chamber 211 of the apparatus 202 by terminating or reducing the flow of the biologic sample through the apparatus 202. While complete flow termination may be difficult to achieve, significant reduction of the flow rate (or slow down of the flow) may enable enough time for deformation analysis to be performed. In some examples, a pulsatory flow might be used to move cells with deformation analysis during flow pause.

As discussed with regards to FIG. 1, the apparatus 202 may cause deformation of the cell 201 by introducing ultrasonic waves into the cell probing chamber 211. More specifically, a standing pressure-wave field may be generated between PIJ actuators 217-1 and 217-2 fired at a frequency in the gigahertz range. As the standing pressure wave applies pressure on the cell 201, the deformability of the cell 201 may be measured (e.g., responsive to the introduction of the ultrasonic waves). To view the cell 201 and measure the deformability, the apparatus 202 may include integrated optics and/or an external imaging system. The integrated optics may include lenses, such as micro-lenses packaged with the microfluidic device, or flat-lenses which are fabricated directly or packaged with the microfluidic capping layer, or imaged through lens-less computational microscopy.

Although FIG. 2 illustrates a cross-shaped microfluidic device and/or apparatus, examples are not so limited. For instance, in various examples, the apparatus includes a fluidic channel, with fluidic pumps disposed on opposing ends to control the flow of a biologic sample therethrough. The apparatus may further include an ultrasound source to perform deformation testing, as discussed herein. The ultrasound source may be an external ultrasound source to generate a standing wave within the fluidic channel, or the ultrasound source may be an integrated ultrasound source to generate the standing wave. As an illustration, the fluidic channel may be a channel with an input and an output on a side opposing the input. The biologic sample may flow along an axis from the input to the output. A PIJ actuator, or a plurality of PIJ actuators may be disposed within the fluidic channel. For instance, a PIJ actuator may be disposed within the fluidic channel and arranged to generate a standing wave traversing the axis of the fluid flow. Additionally and/or alternatively, a plurality of PIJ actuators may be disposed within the fluidic channel and arranged to generate the standing wave traversing the axis of the fluid flow.

Figure 3:
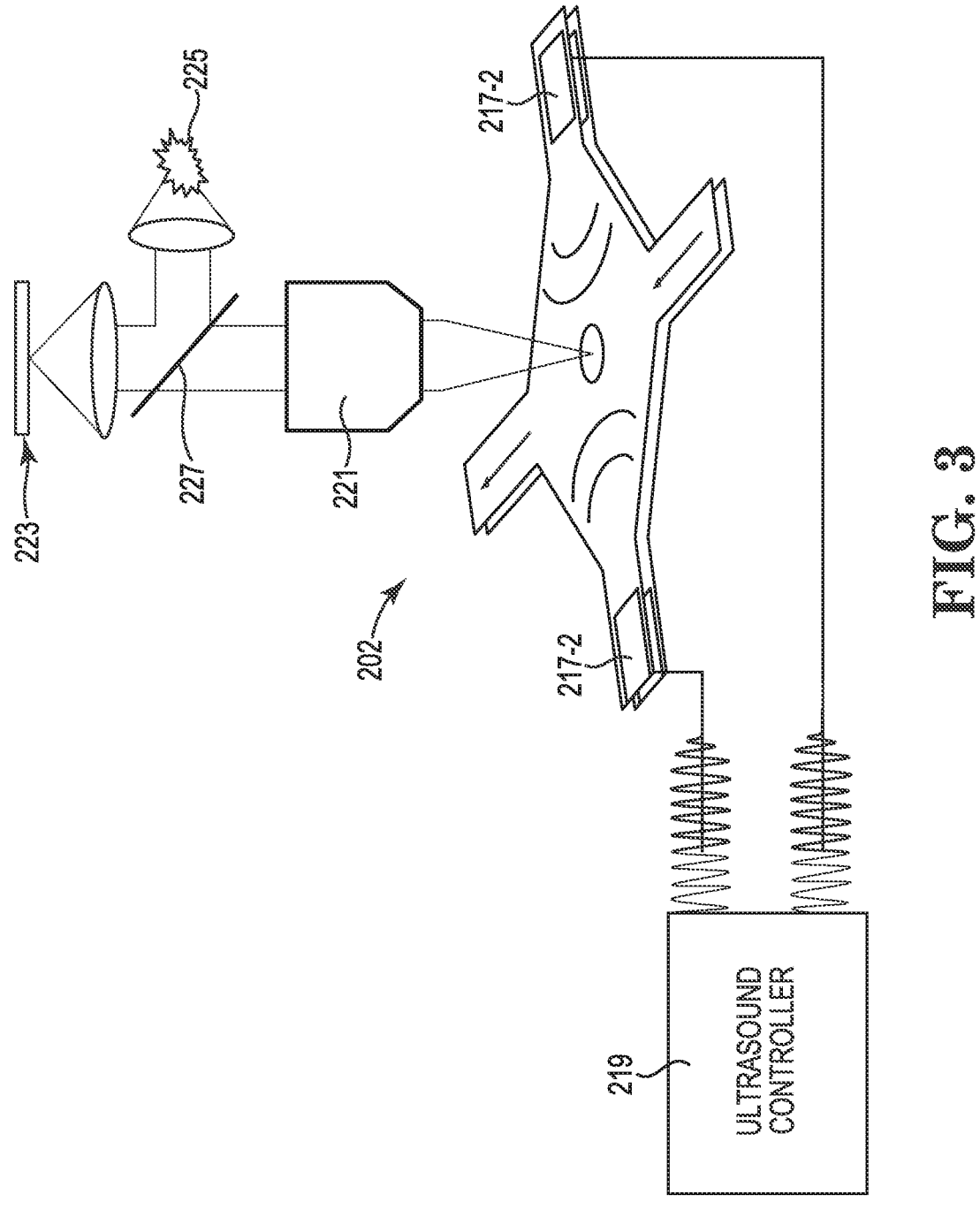
FIG. 3 further illustrates an example apparatus for measuring deformability of a cell, consistent with the present disclosure.

FIG. 3 further illustrates an example apparatus 202 for measuring deformability of a cell, consistent with the present disclosure. More particularly, FIG. 3 illustrates the apparatus 202 with a coupled ultrasound controller 219, and an external imaging system. As illustrated, the ultrasound controller 219 may be coupled to PIJ actuators 217-2 and 217-1. The ultrasound controller 219 may coordinate the simultaneous firing of the PIJ actuators 217-2 and 217-1 with semi-periodic pulses as to create a standing pressure-wave in the chamber 211. In some examples, the ultrasonic waves may be generated using an ultrasonic pressure field using an ultrasonic transducer external to the apparatus 202. Accordingly, in some examples, the apparatus includes a plurality of piezoelectric actuators disposed on opposing ends of a lateral fluidic channel (e.g., channel 215 illustrated in FIG. 2). The ultrasound controller 219 may be communicatively coupled to the PIJ actuators 217-2 and 217-1 (e.g., coupled to the ultrasound source) to control a frequency of the ultrasound waves applied to the cell (e.g., 201 illustrated in FIG. 1).

Also as illustrated in FIG. 3, the apparatus 202 includes an imagining system. For instance, as illustrated in FIG. 3, the imaging system may include an image sensor 223, which may be a charge-couple device (CCD), a complementary metal-oxide-semiconductor (CMOS) imaging device, or any other suitable imaging sensor. The imaging system may further include a light source 225, a dichroic mirror 227, and an objective 221 to visualize the cell 201.

Figure 4:
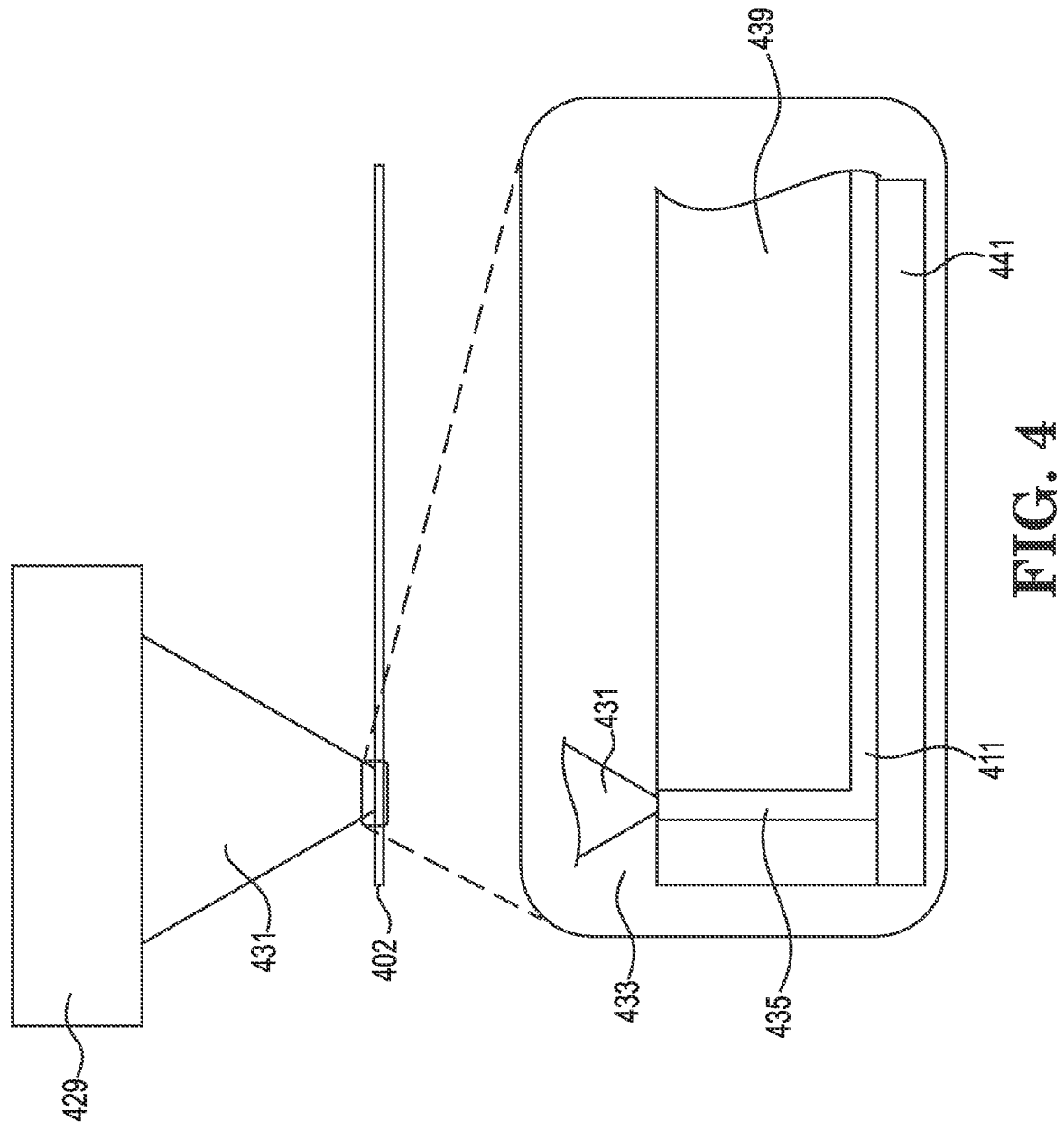
FIG. 4 further illustrates a side profile of a portion of an example apparatus for measuring deformability of a cell, consistent with the present disclosure.

FIG. 4 further illustrates a side profile of a portion of an example apparatus 402 for measuring deformability of a cell, consistent with the present disclosure. More particularly, FIG. 4 illustrates the apparatus 402 with an external ultrasonic wave source. As illustrated in FIG. 4, an ultrasonic pressure field may be generated using an external ultrasonic transducer 429-1 and 429-2. The pressure wave from the ultrasonic transducer may be focused using an ultrasonic horn 431-1 and 432-2 to intensify the pressure wave.

The intensified pressure wave may be delivered to a small via opening, also referred to herein as a coupling port, in the apparatus and/or microfluidic device. For instance, box 433 illustrates an exploded view of a portion of the apparatus 402. As illustrated in FIG. 4, the ultrasound horn 431 may deliver the intensified pressure wave to the via 435. As used herein, the via 435 refers to or includes a channel traversing a silicon top-layer 439 of the apparatus 402. The via 435 is fluidically coupled with the cell probing chamber 411 and does not extend into a base-layer 441 of the apparatus 402. The base-layer 441 may comprise SU-8 or other suitable components. The via is filled with an aqueous solution which we use to probe our cells.

In various examples, the via 435 may be filled with an aqueous solution. The interface between this aqueous solution and the silicon in layer 439 is an interface with a strong difference in wave speed. Thus, the via 435 etched in silicon 439 acts as a waveguide conveying the pressure wave into the cell probing chamber 411.

Figures 5A, 5B:
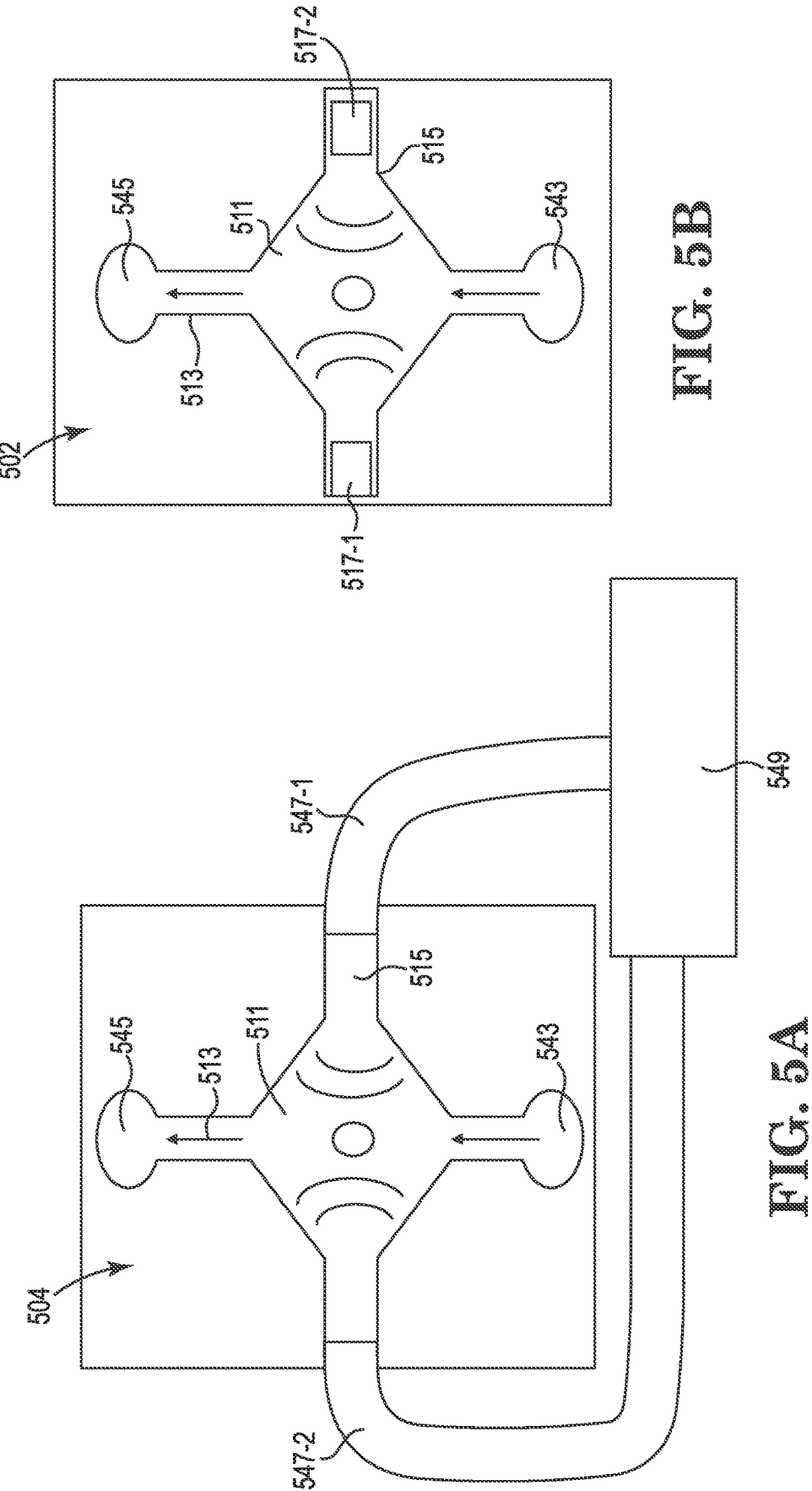
FIGS. 5A and 5B illustrate example apparatuses for measuring deformability of a cell, consistent with the present disclosure.

FIGS. 5A and 5B illustrate example apparatuses for measuring deformability of a cell, consistent with the present disclosure. More particularly, FIGS. 5A and 5B illustrate additional examples of providing ultrasound waves. As illustrated in FIG. 5A, an apparatus 504 for measuring deformability of a cell may include a lateral fluidic channel 515 and a longitudinal fluidic channel 513 disposed orthogonal to the lateral fluidic channel 515. Fluid, including a biologic sample, may be input at fluidic input 543, flow through the apparatus 502 in the direction of the arrow, and exit the apparatus 504 at the fluidic output 545.

In some examples, the flow of fluid is controlled by integrated fluidic pumps. For instance, fluidic pumps may be disposed within channel 515 and within channel 513 (not illustrated in FIG. 5A). The flow within the apparatus 504 may be controlled by individually actuating different fluidic pumps. For instance, to induce flow from fluidic input 543 to fluidic output 545, fluidic pumps near fluidic input 543 may be actuated. To reverse the flow and/or slow the flow of fluid from fluidic input 543 to fluidic output 545, fluidic pumps near fluidic output 545 may be actuated. To stop the flow of fluid, all fluidic pumps may cease firing.

As illustrated in FIG. 5A, piezoelectric elements 517-1 and 517-2 may be disposed on opposing sides of the lateral fluidic channel 515. As discussed herein, the piezoelectric elements 517-1 and 517-2 may create a standing wave within the cell probing chamber 511. In various examples, fluidic pumps may also be disposed within fluidic channel 515. For instance, a fluidic pump (not illustrated) may be disposed near piezoelectric element 517-1, and another fluidic pump (not illustrated) may be disposed near piezoelectric element 517-2. Firing of pumps within fluidic channel 515 may direct a cell along channel 515 between piezoelectric element 517-1 and piezoelectric element 517-2. For instance, in additional examples, a cell may be released from the cell probing chamber 511 by asymmetrically activating a plurality of fluidic pumps in the apparatus 504. In some examples, the integrated fluidic pumps may be thermal inkjet (TIJ) ejectors, among other examples. Additionally and/or alternatively, an external pump or external pumps may be used to induce a fluid flow in the microfluidic device 502.

Each of the lateral fluidic channel 515 and the longitudinal fluidic channel 513 may be actuated by a different respective set of fluidic pumps. The cell probing chamber 511 may be disposed at an intersection of the lateral fluidic channel 515 and the longitudinal fluidic channel 513. As described herein, the cell probing chamber 511 may hold a single cell from a biologic sample for deformation testing. An ultrasound source may allow for perform deformation testing on the cell by applying a pressure field to the cell in the cell probing chamber 511. For instance, piezoelectric elements 517-1 and 517-2 may actuate so as to form a standing wave within cell probing chamber 511. An integrated imaging system and/or an external imaging system may allow for the imaging and measurement of deformation of the cell, responsive to application of the standing wave.

FIG. 5B further illustrates an example apparatus 502 including an external ultrasound generator. As illustrated in FIG. 5B, waveguide channels 547-1 and 547-2 may be fluidically coupled to the ends of channel 515. Each of waveguide channels 547-1 and 547-2 may be coupled to an ultrasound generator 549. The ultrasound waves generated by the ultrasound generator 549 may travel through the waveguide channels 547-1 and 547-2 and generate a standing wave in the cell probing chamber 511.

Figure 6:
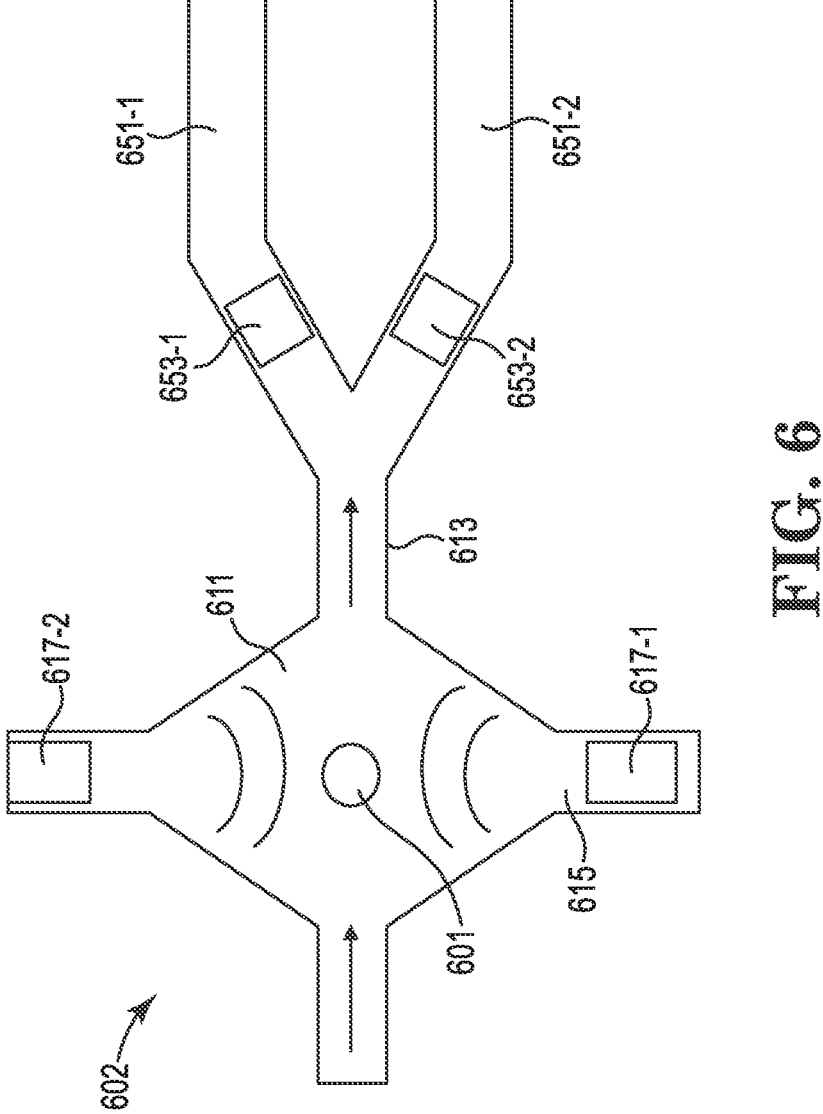
FIG. 6 further illustrates an example apparatus for measuring deformability of a cell, consistent with examples of the present disclosure.

FIG. 6 further illustrates an example apparatus 602 for measuring deformability of a cell, consistent with examples of the present disclosure. As illustrated in FIG. 6, a plurality of channels 651-1 and 651-2 may be fluidically coupled to the cell probing chamber 611 to sort and concentrate cells after deformation testing. For instance, as the properties of the cell 601 are determined, one of a plurality of pumps 653-1 and 653-1 may fire to pull the cell 601 into the associated channel, 651-1 or 651-2, respectively. As an example, if a deformability of the cell 601 is detected to be above a particular threshold, then the cell 601 may be drawn into channel 651-1 by firing pump 653-2 to push the cell 601 into channel 651-1. Similarly, if a deformability of the cell 601 is detected to be below a particular threshold, then the cell 601 may be drawn into channel 651-2 by firing pump 653-1 to push the cell 601 into channel 651-2. Additionally and/or alternatively, piezoelectric elements 617-1 and 617-2 may fire to push the cell 601 into channel 651-2 or channel 651-1. Although FIG. 6 illustrates two fluidic channels fluidically coupled to the cell probing chamber 611, examples are not so limited, and any number of fluidic channels may be coupled to the cell probing chamber 611. Multiple channels may be of particular interest for cell sorting and concentration in different cell collectors.

Figure 7:
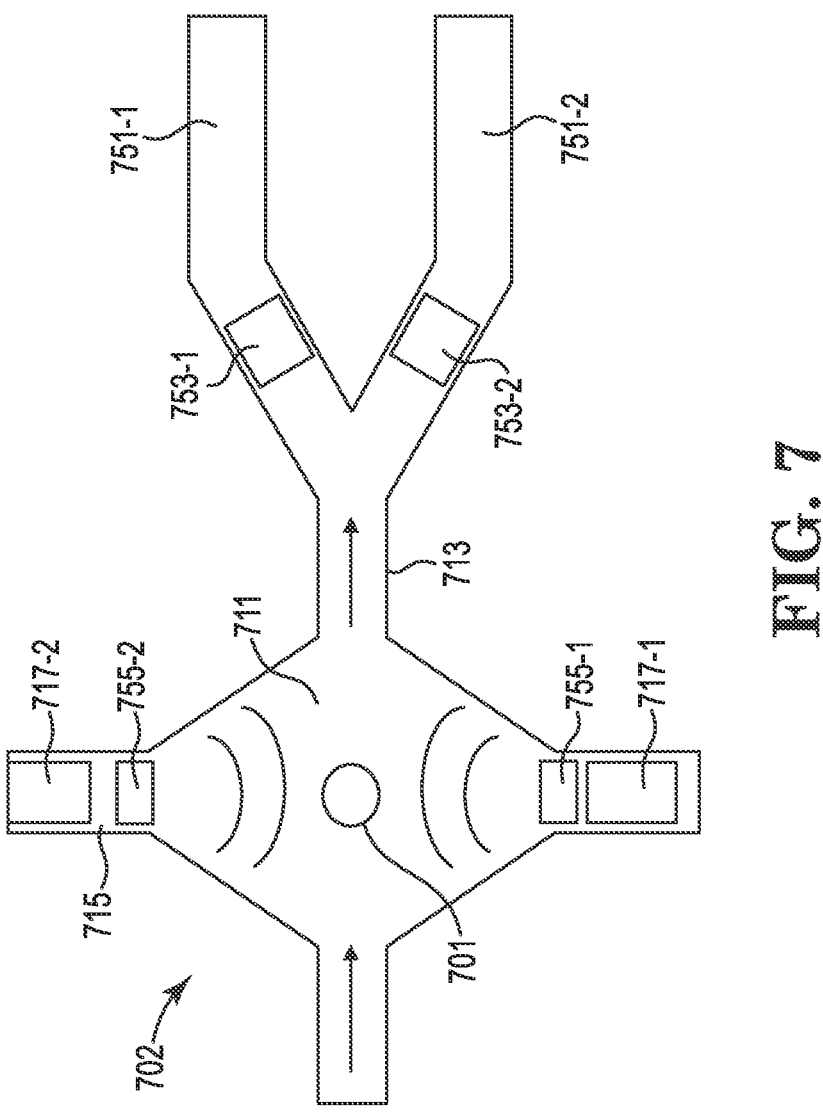
FIG. 7 further illustrates an example apparatus for measuring deformability of a cell, consistent with examples of the present disclosure.

FIG. 7 further illustrates an example apparatus 702 for measuring deformability of a cell, consistent with examples of the present disclosure. Similar to FIG. 6, the apparatus 702 includes a plurality of channels 751-1 and 751-2 may be fluidically coupled to the cell probing chamber 711 to sort cells after deformation testing. For instance, as the properties of the cell 701 are determined, one of a plurality of pumps 753-1 and 753-1 may fire to pull the cell 701 into the associated channel, 751-1 or 751-2, respectively. Additionally and/or alternatively, piezoelectric elements 717-1 and 717-2 may fire to push the cell 701 into channels 751-1 or 751-2. Moreover, TIJ resistors 755-1 and 755-2 may be disposed adjacent to piezoelectric elements 717-1 and 717-2. The TIJ resistors 755-1 and 755-2 may also be fired to direct the flow of the cell 701 into one of channels 751-1 or 751-2. Although FIG. 7 illustrates two fluidic channels fluidically coupled to the cell probing chamber 711, examples are not so limited, and any number of fluidic channels may be coupled to the cell probing chamber 711.

Figure 8:
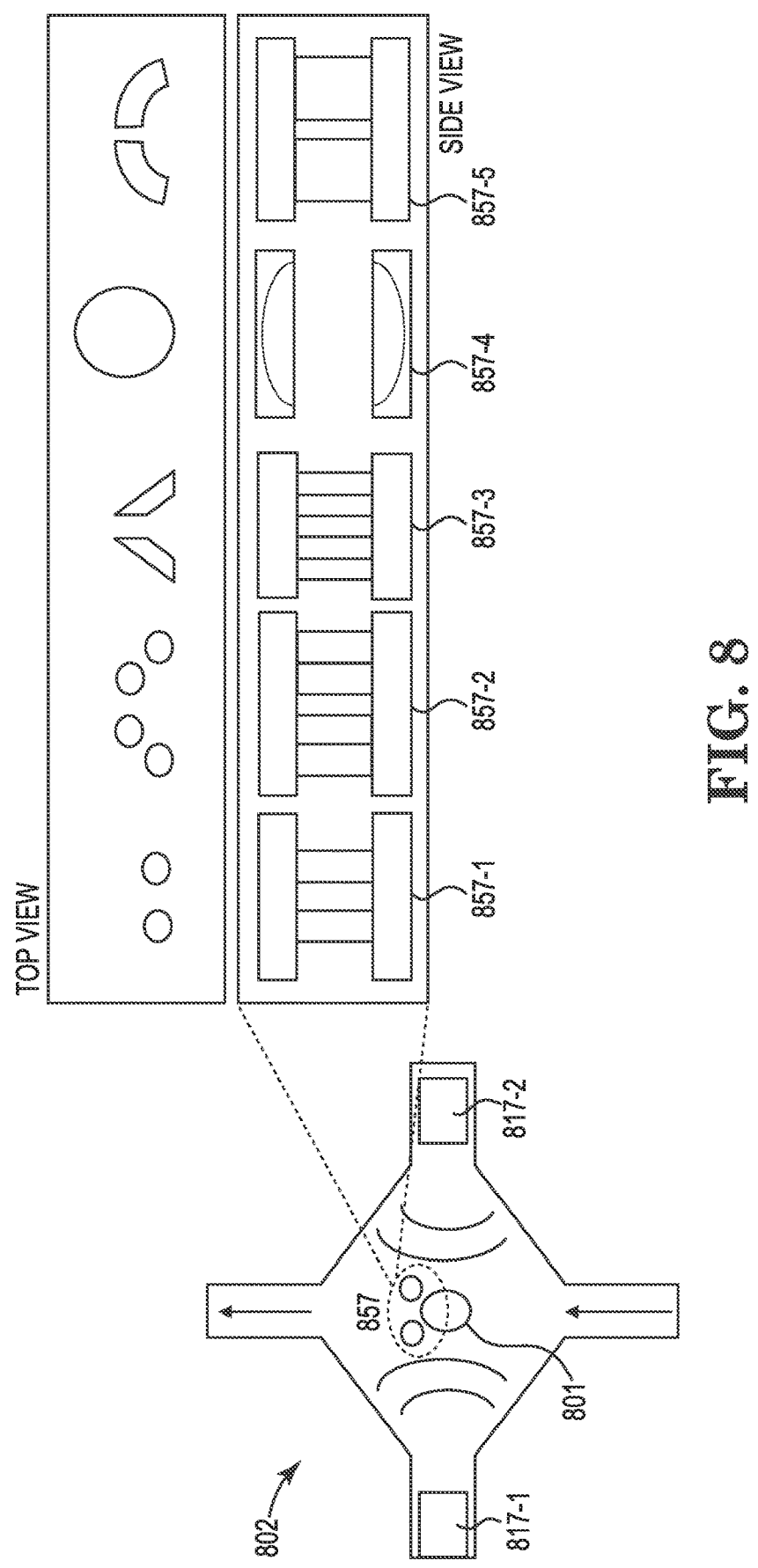
FIG. 8 illustrates an example apparatus for measuring deformability of a cell including barriers to contain a cell, consistent with examples of the present disclosure.

FIG. 8 illustrates an example apparatus 802 for measuring deformability of a cell including barriers to contain a cell, consistent with examples of the present disclosure. For instance, in various examples, apparatus 802 may include a barrier 857 to contain the cell 801. Examples 857-1, 857-2, 857-3, 857-4 and 857-5 illustrate various designs of a barrier 857 that may be used. As illustrated, barrier 857-1 may include two pillars disposed orthogonal to the flow of the biologic sample to trap the cell 801 for measuring deformability. Once measurements are obtained, piezoelectric elements 817-1 and/or 817-2 may actuate to move the cell 801 around the barrier 857-1.

As a further example, a pillar trap 857-2 may be disposed orthogonal to the flow of the biologic sample. Similar to the two pillars illustrated in 857-1, the pillar trap 857-2 may include a plurality of vertically aligned pillars to trap the cell 801 for measuring deformability. Once measurements are obtained, piezoelectric elements 817-1 and/or 817-2 may actuate to move the cell 801 around the barrier 857-2.

In yet another example, a funnel 857-3 may be disposed orthogonal to the flow of the biologic sample. The funnel 857-3 may include two tapered members, vertically aligned orthogonal to the flow of the biologic sample. The tapered members may trap the cell 801 for measuring deformability. Once measurements are obtained, piezoelectric elements 817-1 and/or 817-2 may actuate to move the cell 801 around the barrier 857-3.

Furthermore, a depression 857-4 may be disposed orthogonal to the flow of the biologic sample. The depression 857-4 may include a recessed portion of the substrate and lid of the apparatus 802. The depression 857-4 may trap the cell 801 for measuring deformability. Once measurements are obtained, piezoelectric elements 817-1 and/or 817-2 may actuate to move the cell 801 out of the depression 857-4.

Yet further, a wall 857-5 may be disposed orthogonal to the flow of the biologic sample. The wall 857-5 may include a plurality of curved orthogonal pillars within the apparatus 802. The wall 857-5 may be disposed orthogonal to the flow of the biologic sample and may trap the cell 801 for measuring deformability. Once measurements are obtained, piezoelectric elements 817-1 and/or 817-2 may actuate to move the cell 801 out of the depression 857-5.

Although 857-1, 857-2, 857-3, 857-4, and 857-5 illustrate different kinds of structures that can facilitate the trapping of the cell 801 in the cell probing chamber, different and/or additional barriers 857 may be used. In any scenario, the cell 801 may be released from the barrier 857 by reversing the flow momentarily and providing a lateral flow simultaneously by actuating the piezoelectric elements 817-1 and/or 817-2 in an asymmetric way, before re-establishing the flow in the direction illustrated.

Figures 9A, 9B:
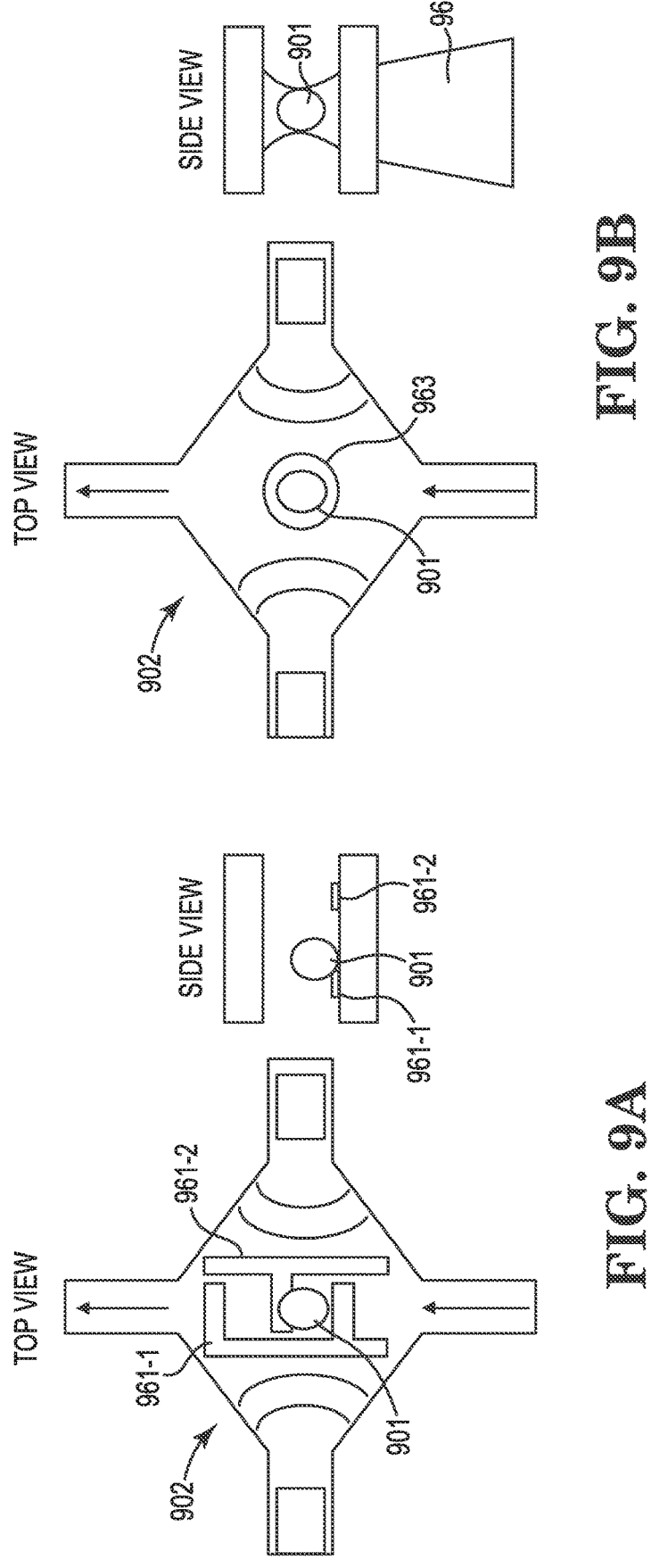
FIGS. 9A and 9B illustrate example apparatuses for measuring deformability of a cell including non-mechanical mechanisms to contain a cell, consistent with examples of the present disclosure.

FIGS. 9A and 9B illustrate example apparatuses 902 for measuring deformability of a cell including non-mechanical mechanisms to contain a cell 901, consistent with examples of the present disclosure. More particularly, FIG. 9A illustrates an example apparatus 902 for measuring deformability of a cell including three-dimensional electrodes 961-1 and 961-2, consistent with the present disclosure. Using a dielectrophoresis (DEP)-based cell-separation method, three-dimensional electrodes 961-1 and 961-2 may be disposed on the substrate of the apparatus 902 and may hold the cell 901 at a point of high electric field gradient. Accordingly, in some examples, the apparatus 902 may include a plurality of electrodes 961-1 and 961-2 disposed in a substrate of the cell probing chamber, the plurality of electrodes 961-1 and 961-2 to hold the cell 901 in the cell probing chamber by dielectrophoresis.

Similarly, FIG. 9B illustrates an example apparatus 902 for measuring deformability of a cell including a laser beam gradient 963, consistent with the present disclosure. In such examples, the laser beam gradient 963 may be created by a laser optical system. The laser beam gradient 963 forms a single-beam gradient force trap to hold the cell 901 in the cell probing chamber. The cell 901 may be released from the cell probing chamber by terminating the electric field in FIG. 9A, or by terminating the laser beam gradient in FIG. 9B.

Figure 10:
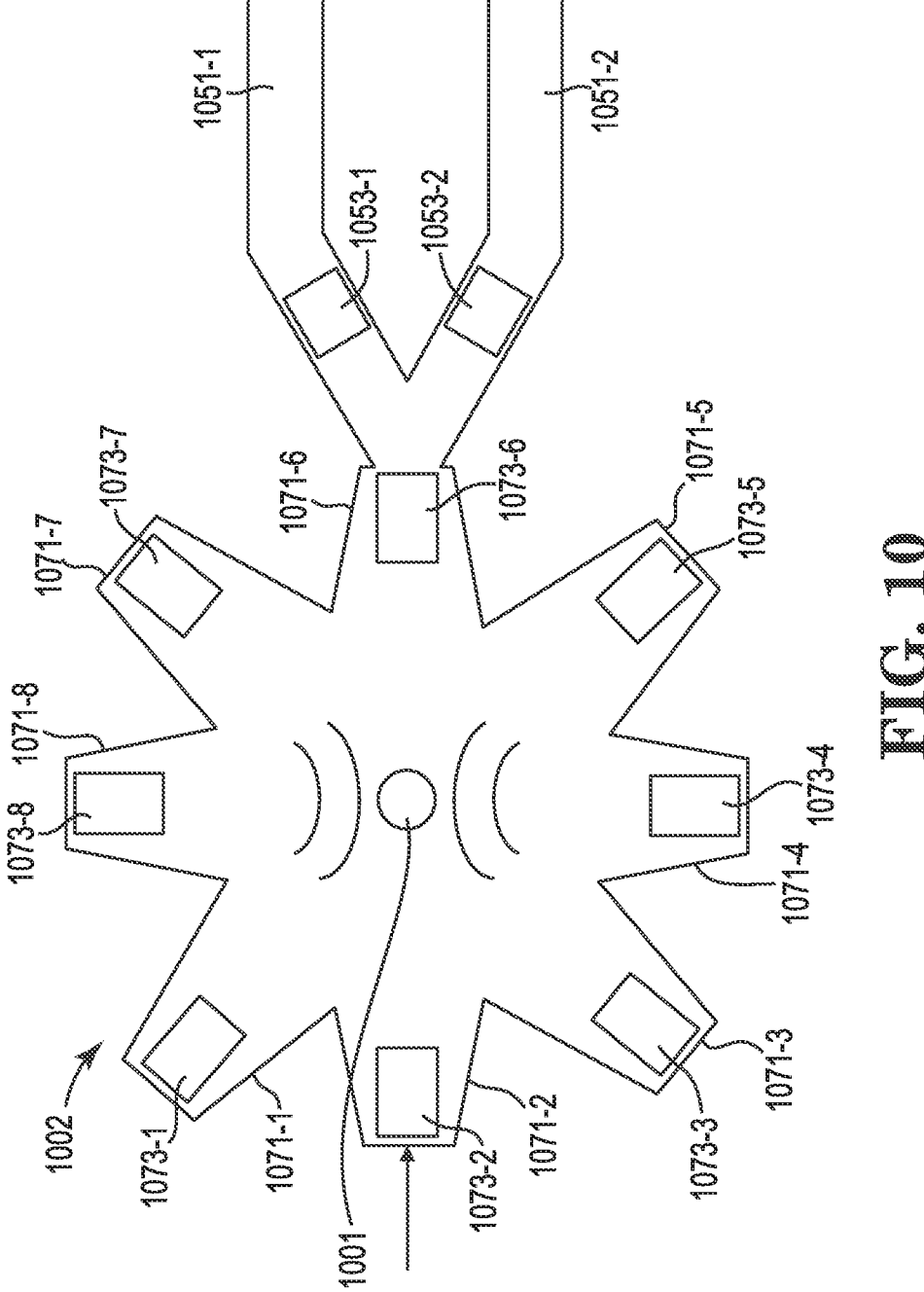
FIG. 10 illustrates an example apparatus for measuring deformability of a cell, consistent with the present disclosure.

FIG. 10 illustrates an example apparatus 1002 for measuring deformability of a cell, consistent with the present disclosure. As illustrated in FIG. 10, a plurality of diagonal channels 1071-1, 1071-2, 1071-3, 1071-4, 1071-5, 1071-6, 1071-7, and 1071-8 (referred to collectively as diagonal channels 1071) may be fluidically coupled to the cell probing chamber. Each diagonal channel 1071 may further include a piezoelectric element 1073-1, 1073-2, 1073-3, 1073-4, 1073-5, 1073-6, 1073-7, and 1073-8 (referred to collectively as piezoelectric elements 1073). The piezoelectric elements 1073 may provide a variety of combinations for generating a standing ultrasound wave, and/or provide a variety of combinations for moving the cell 1001 through the apparatus 1002. For instance, a subset of the piezoelectric elements 1073 may be selected for firing to create the standing ultrasound wave. Additionally and/or alternatively, a subset of the piezoelectric elements 1073 may be selected for moving the cell 1001 into channels 1051-1 or 1051-2. Moreover, pumps 1053-1 and/or 1053-2 may assist in directing the flow of the cell 1001 into a respective channel.

Figure 11:
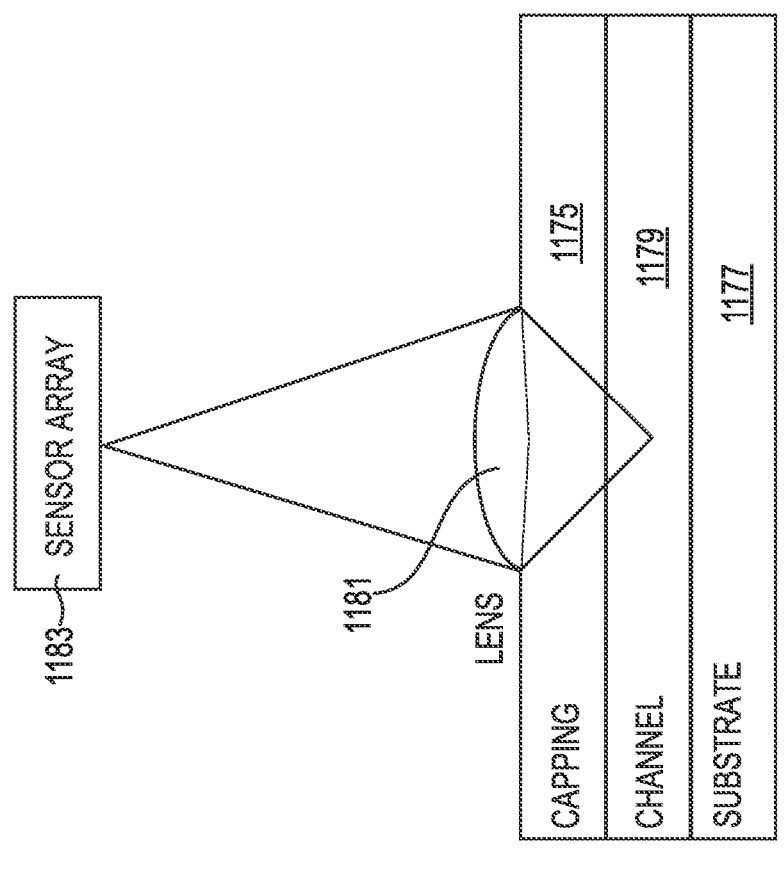
FIG. 11 illustrates an example apparatus for measuring deformability of a cell, consistent with the present disclosure.

FIG. 11 illustrates an example apparatus 1102 for measuring deformability of a cell, consistent with the present disclosure. Particularly, FIG. 11 illustrates an apparatus 1102 including an integrated optics system. As illustrated in FIG. 11, the apparatus 1102 may include a lateral fluidic channel 1115, a longitudinal fluidic channel 1113, and a cell probing chamber 1111. The cell probing chamber 1111 may include a transparent lid 1175 disposed over a base substrate 1177 to form a channel 1179 therethrough. An integrated lens 1181 may be disposed on the transparent lid 1175 of the cell probing chamber 1111. The integrated lens 1181 may focus light from the cell 1101 in the cell probing chamber 1111 to a sensor array 1183.

The integrated lens 1181 could comprise a plurality of materials. For instance, the integrated lens 1181 could comprise a zone plate, a Fresnel lens, metasurfaces, or other suitable lenses and/or micro-lenses for a variety of imaging modalities and optical configurations (e.g., infinity corrected, point-to-point magnification, integrated source, fluorescence, etc.). If a flat lens is used, the sensor can be in close proximity to the channel and substrate to create a compact package.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. Therefore, it is intended that this disclosure be limited only by the claims and the equivalents thereof.

The invention claimed is:

1. An apparatus, comprising:
a fluidic channel actuated by a set of fluidic pumps;
a cell probing chamber disposed in the fluidic channel, wherein the cell probing chamber is to hold a single cell from a biologic sample for deformation testing; and
an ultrasound source acoustically coupled to the cell probing chamber through a via coupled with the cell probing chamber, the ultrasound source configured to perform deformation testing on the cell by applying, through the via, a pressure field to the cell in the cell probing chamber,
wherein the via is formed through a silicon top layer of the apparatus, the via to fill with an aqueous acoustic transmission medium and terminating at the cell probing chamber without extending into a base layer of the apparatus.

2. The apparatus of claim 1, wherein the ultrasound source includes a plurality of piezoelectric actuators disposed on opposing ends of the fluidic channel.

3. The apparatus of claim 1, further including an ultrasound controller communicatively coupled to the ultrasound source to control a frequency of the ultrasound waves applied to the cell.

4. An apparatus, comprising:
a lateral fluidic channel and a longitudinal fluidic channel disposed orthogonal to the lateral fluidic channel, wherein each of the lateral fluidic channel and the longitudinal fluidic channel are actuated by a different respective set of fluidic pumps;
a cell probing chamber disposed at an intersection of the lateral fluidic channel and the longitudinal fluidic channel, wherein the cell probing chamber is to hold a single cell from a biologic sample for deformation testing;
an ultrasound source acoustically coupled to the cell probing chamber through a via coupled with the cell probing chamber, the ultrasound source configured to perform deformation testing on the cell by applying, through the via, a pressure field to the cell in the cell probing chamber; and
a plurality of channels fluidically coupled to the cell probing chamber to sort cells after deformation testing.

5. The apparatus of claim 4, wherein the cell probing chamber includes a barrier to contain the cell, the barrier including two pillars disposed orthogonal to a flow of the biologic sample, a pillar trap disposed orthogonal to the flow of the biologic sample, a funnel disposed orthogonal to the flow of the biologic sample, a depression in a substrate of the cell probing chamber, a wall disposed orthogonal to the flow of the biologic sample, or combinations thereof.

6. The apparatus of claim 4, including a plurality of electrodes disposed in a substrate of the cell probing chamber, the plurality of electrodes to hold the cell in the cell probing chamber by dielectrophoresis.

7. The apparatus of claim 4, wherein the cell probing chamber includes a laser optical system to form a single-beam gradient force trap to hold the cell in the cell probing chamber.

8. The apparatus of claim 4, wherein the lateral fluidic channel, the longitudinal fluidic channel, and the cell probing chamber include a transparent lid disposed over a base substrate to form a channel therethrough.

9. The apparatus of claim 8, further including an integrated lens disposed on the transparent lid of the cell probing chamber, the integrated lens to focus light from a sensor array on the cell in the cell probing chamber.

10. The apparatus of claim 4, further including a plurality of diagonal channels fluidically coupled to the cell probing chamber, each diagonal channel including a fluidic pump to direct a flow of the biologic sample through the apparatus.

* * * * *